US00PP27688P3

(12) United States Plant Patent
Bergman

(10) Patent No.: US PP27,688 P3
(45) Date of Patent: Feb. 21, 2017

(54) ***CHRYSANTHEMUM* PLANT NAMED 'CIDZ0068'**

(50) Latin Name: *Chrysanthemum×morifolium*
Varietal Denomination: CIDZ0068

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,151

(22) Filed: Aug. 6, 2015

(65) Prior Publication Data

US 2016/0057909 P1 Feb. 25, 2016

Related U.S. Application Data

(60) Provisional application No. 62/039,706, filed on Aug. 20, 2014.

(51) Int. Cl.
*A01H 5/02* (2006.01)

(52) U.S. Cl.
USPC ..... Plt./295

(58) Field of Classification Search
USPC ..... Plt./295
CPC ..... A01H 5/0225
See application file for complete search history.

*Primary Examiner* — Kent L Bell
(74) *Attorney, Agent, or Firm* — Dale Skalla

(57) ABSTRACT

A new *Chrysanthemum* plant named 'CIDZ0068' particularly distinguished by the stable yellow-colored, daisy-type inflorescences, and an excellent plant strength in combination with a flowering response time of 8 weeks when grown under short-day conditions.

1 Drawing Sheet

Latin name of the genus and species of the plant claimed: *Chrysanthemum×morifolium.*

Varietal denomination: 'CIDZ0068'.

BACKGROUND OF THE NEW PLANT

The present invention comprises a new *Chrysanthemum*, botanically known as *Chrysanthemum×morifolium,* and hereinafter referred to by the variety name 'CIDZ0068'.

'CIDZ0068' is a product of a planned breeding program. The new cultivar has stable yellow-colored, daisy-type inflorescences, and an excellent plant strength in combination with a flowering response time of 8 weeks when grown under short-day conditions.

'CIDZ0068' originates as a natural whole plant mutation discovered among flowering plants of the variety 'CIDZ0014' growing in a greenhouse in Gilroy, California in August 2011.

The parent is the proprietary plant 'CIDZ0014', disclosed in U.S. Plant Pat. No. 23,111, and having inflorescences of a golden-bronze hue under usual conditions, while it is similar to 'CIDZ0068' in all other characteristics.

The first act of asexual reproduction of 'CIDZ0068' was accomplished when vegetative cuttings were propagated from the initial selection in November 2011 in a greenhouse in Gilroy, Calif.

BRIEF SUMMARY OF INVENTION

Horticultural examination of plants grown from cuttings of the plant initiated April 2012, and continuing thereafter, has demonstrated that the combination of characteristics as herein disclosed for 'CIDZ0068' are firmly fixed and are retained through successive generations of asexual reproduction.

'CIDZ0068' has not been observed under all possible environmental conditions. The phenotype may vary significantly with variations in environment such as temperature, light intensity, and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0068' with colors being as true as possible with an illustration of this type.

Figure 1:
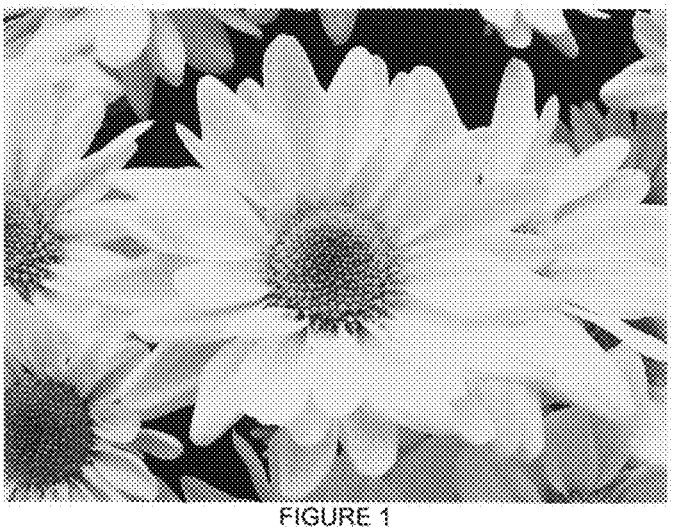
Figure 2:
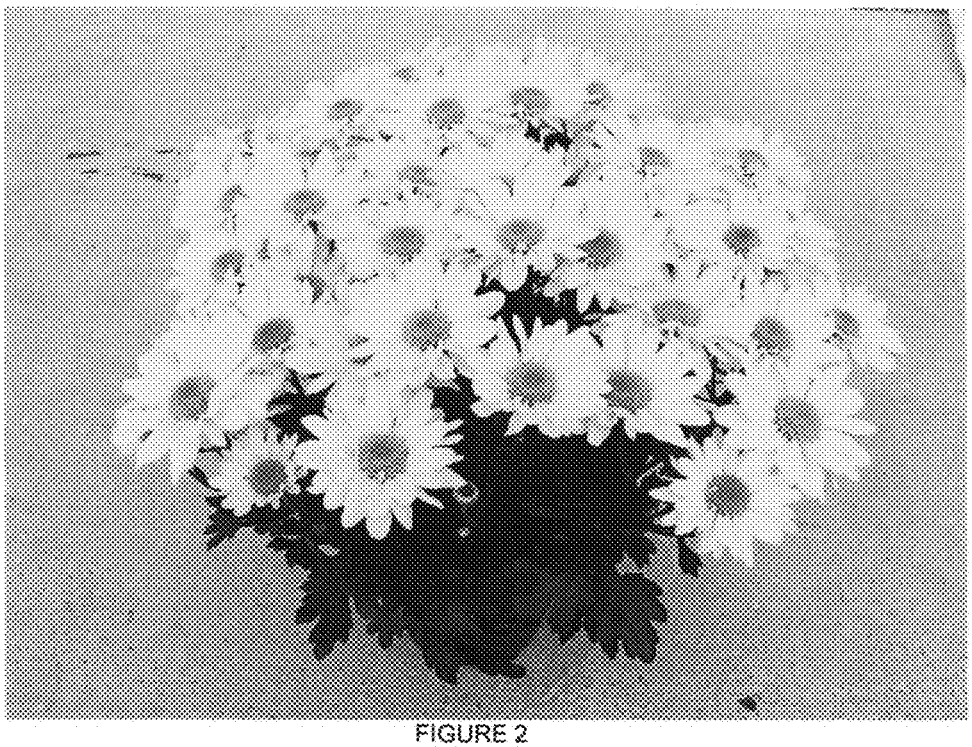

The photographic drawings show in FIG. 1 a close-up of an inflorescence, and in FIG. 2, a flowering potted plant.

DETAILED BOTANICAL DESCRIPTION

The plant descriptions and measurements were taken indoors in Nipomo, Calif. in August 2014 on about 11 week old plants. Unrooted cuttings had been planted, 4 plants per pot, in 6 inch pots on May 24, 2014. The plants were pinched and moved to short days on Jun. 16, 2014 to induce flowering.

The aforementioned photographs: FIGS. 1 and 2 were taken in Nipomo, Calif., in May 2013, and showing an 11 week old plant from a trial, in which flowering had been induced by applying black cloth. Unrooted cuttings had been planted into in a 6 inch pot in February 2013.

Color references are made to The Royal Horticultural Society Colour Chart (R.H.S.) 2001.

TABLE 1

DIFFERENCES BETWEEN THE NEW VARIETY 'CIDZ0068' AND A MOST SIMILAR VARIETY

| | 'CIDZ0068' | 'CIDZ0014' (U.S. Plant Pat. No. 23,111) |
|---|---|---|
| Flower color: | Yellow, near RHS 7B | Golden bronze, RHS 3B, largely overlain with 17B-17C tones |
| Flower color, stability: | Yellow under all conditions | May turn lighter under extreme temperature conditions |
| Plant habit and flowering response | Same | Same |

Plant:

*Form, growth and habit.*—Herbaceous pot-type, stems upright, freely branching, strong and moderately vigorous growth habit.

*Plant height.*—24.0-26.0 cm.

*Plant height (inflorescence included).*—About 30.0 cm.

*Plant width.*—22.0-25.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Closest to RHS 147B.

*Mature, leaf color, upper surface.*—Closest to RHS 147A.

*Lower surface.*—Closest to RHS 147B.

*Length.*—7.0-7.8 cm.

*Width.*—5.5-6.3 cm.

*Shape.*—Ovate.

*Base shape.*—Attenuate.

*Apex shape.*—Cuspidate.

*Margin.*—Palmately lobed; irregularly incised, somewhat serrate.

*Texture, upper surface.*—Bifid T-shaped hairs.

*Lower surface.*—Bifid T-shaped hairs.

*Color of veins, upper surface.*—RHS 147B.

*Color of veins, lower surface.*—RHS 147C.

*Pattern of veining.*—Palmate.

*Petiole color.*—RHS 147B.

*Length.*—1.7-2.2 cm.

*Diameter.*—0.3-0.4 cm.

*Texture.*—Bifid T-shaped hairs.

Stem:

*Quantity of main branches per plant.*—4-5.

*Color of stem.*—RHS 146B but appears lighter due to hairs.

*Length of stem.*—About 24 cm.

*Diameter.*—0.4-0.6 cm.

*Length of internodes.*—0.5-4.0 cm.

*Texture.*—Bifid T-shaped hairs.

*Color of peduncle.*—RHS 146B but appears lighter due to hairs.

*Length of peduncle.*—4.5-9.0 cm.

*Peduncle diameter.*—0.25-0.35 cm.

*Texture.*—Bifid T-shaped hairs.

Inflorescence:

*Type.*—Compositae type, solitary daisy-type inflorescences borne terminally above foliage, ray florets arranged acropetally on a capitulum.

*Quantity of short days to flowering (response time).*—8 weeks.

*Natural season flowering.*—Not determined on this variety.

*Quantity of inflorescences per plant.*—90-110.

*Lastingness of individual blooms on the plant.*—4 weeks.

*Fragrance.*—Slightly spicy.

Bud (just when opening/showing color):

*Color.*—Closest to RHS 151D.

*Length.*—1.0-1.2 cm.

*Width.*—1.2-1.4 cm.

*Shape.*—Oblate.

Immature inflorescence:

*Diameter.*—4.5-5.5 cm.

*Color of ray florets, upper surface.*—Closest to RHS 9A.

*Lower surface.*—Closest to RHS 7B.

Mature inflorescence:

*Diameter.*—6.8-7.4 cm.

*Depth.*—1.8-2.2 cm.

*Total diameter of disc.*—1.3 cm.

*Receptacle color.*—RHS 147B.

*Receptacle height.*—0.6 cm.

*Receptacle diameter.*—1.8-2.0 cm.

Ray florets:

*Average quantity of florets.*—27-35 in 3 whorls.

*Color of florets, upper surface.*—Closest to RHS 7B.

*Lower surface.*—Closest to RHS 7B.

*Length.*—2.6-3.3 cm.

*Width.*—0.9-1.1 cm.

*Shape.*—Elongated oblong.

*Apex shape.*—Rounded to slightly emarginate.

*Margin.*—Entire.

*Texture, upper surface.*—Smooth, glabrous, velvety.

*Lower surface.*—Smooth, glabrous, velvety.

Disc florets:

*Average quantity of florets.*—Approximately 220.

*Color of florets.*—RHS 145D basally with a RHS 12B apex.

*Length.*—8 mm.

*Width.*—2 mm.

*Shape.*—Tubular, elongated.

*Apex shape.*—Acute, 5 pointed.

Phyllaries:

*Quantity.*—28-33.

*Color, upper surface.*—RHS 137B.

*Lower surface.*—RHS 137A.

*Length.*—0.6-0.9 cm.

*Width.*—0.2 cm.

*Shape.*—Lanceolate.

*Apex shape.*—Acute.

*Base.*—Fused.

*Margins.*—Entire; slightly papery.

*Texture, upper surface.*—Glabrous.

*Lower surface.*—Bifid T-shaped hairs.

Reproductive organs:

*Pistil.*—1, found on both types of florets.

*Length.*—0.5-0.6 cm.

*Style color.*—RHS 1C but translucent looking.

*Style length.*—0.4 cm.

*Stigma color.*—RHS 14B.
*Stigma shape.*—Bi-parted.
*Ovary color.*—Not observed.
*Stamens.*—4, found only on the disc florets.
*Color of filaments.*—RHS 155C.
*Length filaments.*—0.2-0.3 cm.
*Anther color.*—RHS 15A.
*Anther length.*—0.1 cm.
*Anther shape.*—Oblong.
*Color of pollen.*—RHS 17A.
*Pollen amount.*—Moderate.

Fertility/seed set: Has not been observed to date.
Disease/pest resistance: Has not been observed to date.

What is claimed is:

1. A new and distinct variety of *Chrysanthemum* plant named 'CIDZ0068' substantially as illustrated and described herein.

* * * * *